United States Patent
Känsäkoski et al.

(10) Patent No.: US 6,717,148 B2
(45) Date of Patent: Apr. 6, 2004

(54) METHOD AND APPARATUS FOR MEASURING COATING

(75) Inventors: Markku Känsäkoski, Oulu (FI);
Markku Mäntylä, Kangasala (FI);
Jussi Tenhunen, Oulunsalo (FI)

(73) Assignee: Metso Automation Oy, Helsinki (FI)

( * ) Notice: Subject to any disclaimer, the term of this patent is extended or adjusted under 35 U.S.C. 154(b) by 46 days.

(21) Appl. No.: 10/216,009

(22) Filed: Aug. 9, 2002

(65) Prior Publication Data

US 2003/0047135 A1 Mar. 13, 2003

Related U.S. Application Data

(63) Continuation of application No. PCT/FI01/00113, filed on Feb. 8, 2001.

(30) Foreign Application Priority Data

Feb. 10, 2000 (FI) .............................................. 20000282

(51) Int. Cl.$^7$ ........................ G01N 21/25; G01N 21/34
(52) U.S. Cl. ............................ 250/339.11; 250/339.12; 250/341.8; 250/339.1; 250/339.09; 250/341.5; 250/351; 250/353
(58) Field of Search ................... 250/339.11, 339.12, 250/341.8, 339.09, 341.5, 351, 353

(56) References Cited

U.S. PATENT DOCUMENTS

| | | | | |
|---|---|---|---|---|
| 4,345,840 A | * | 8/1982 | Goetz et al. ................ | 356/407 |
| 4,631,408 A | * | 12/1986 | Zelmanovic et al. .. | 250/339.11 |
| 4,965,452 A | * | 10/1990 | Sturm .................... | 250/339.11 |
| 5,250,811 A | | 10/1993 | Lippert et al. | |
| 5,276,327 A | | 1/1994 | Bossen et al. | |
| 5,308,981 A | * | 5/1994 | Perten .................... | 250/339.11 |
| 5,338,361 A | * | 8/1994 | Anderson et al. ........... | 118/689 |
| 5,455,422 A | * | 10/1995 | Anderson et al. ......... | 250/341.1 |
| 5,659,397 A | * | 8/1997 | Miller et al. ................ | 356/446 |
| 5,745,243 A | * | 4/1998 | Wilcox et al. .............. | 356/419 |
| 5,795,394 A | | 8/1998 | Belotserkovsky et al. | |
| 5,818,045 A | * | 10/1998 | Mark et al. ............ | 250/339.12 |
| 5,914,490 A | | 6/1999 | Sumén et al. | |
| 6,433,338 B1 | * | 8/2002 | Nordbryhn et al. .... | 250/339.12 |

FOREIGN PATENT DOCUMENTS

| EP | 0 548 582 A1 | 6/1993 | | |
|---|---|---|---|---|
| EP | 0 943 912 A1 | 9/1999 | | |
| FI | 970612 | 8/1998 | | |
| WO | WO 9836264 A1 | * 8/1998 | .......... | G01N/21/35 |
| WO | WO 99/41590 | 8/1999 | | |

* cited by examiner

Primary Examiner—Albert Gagliardi
(74) Attorney, Agent, or Firm—Alston & Bird LLP

(57) ABSTRACT

The invention relates to a method and an apparatus for measuring a coating from paper or board. The measurement is carried out by one detector at different times or by two detectors simultaneously. IR radiation directed at the coating and radiation emerging from the coating are chopped synchronously in blocks. A wavelength band sensitive and insensitive to the absorption are bandpass filtered and measured in both the MIR and NIR region. The absorption strength is measured in a digital signal processing block by comparing the radiation sensitive to absorption to the radiation insensitive to absorption, and the amount of each coating component is determined in the digital signal processing block on the basis of the absorption strength.

33 Claims, 6 Drawing Sheets

METHOD AND APPARATUS FOR MEASURING COATING

CROSS-REFERENCE TO RELATED APPLICATIONS

This application is a Continuation of International Application PCT/FI01/00113 filed on the 8$^{th}$ of February 2001 which designated the U.S. and was published under PCT Article 21(2) in English, and which is hereby incorporated herein in its entirety by reference.

BACKGROUND OF THE INVENTION

1) Field of the Invention

The invention relates to measuring a paper or board coating. Particularly the invention relates to measuring the coating by means of IR radiation.

2) Description of Related Art

Measuring a paper or board coating is an important part of the manufacturing process of paper or board, because an appropriate coating improves, for example, printability, gloss and color of paper. Instead of applying only one coating layer, the coating can be performed several times using several different materials. Coating materials include binders and coating pigments, and some of the coating components that are used include kaolin, calcium carbonate, talc, gypsum, latex, starch, many synthetic binders and special coatings, such as silicon.

A prior art coating system is described in U.S. Pat. No. 5,795,394, which is incorporated herein by reference. This coating system concentrates on measuring calcium carbonate and controlling the coating in the MIR region. In the solution of the publication, MIR radiation is directed at a coated substrate at two separate wavelength bands, one of which is sensitive to the substrate and the other is sensitive both to the substrate and to calcium carbonate. On the basis of these different wavelength band strengths, the amount of calcium carbonate is measured, and the amount of coating is adjusted by means of the measured calcium carbonate. As far as measurements of other components are concerned, the publication mentions the measurement of kaolin, and also the measurement of paper moisture. The problem of the solution given in the publication is that the amount of only a few components (mainly that of calcium carbonate) used in the coating can be measured, although a large number of coating materials can be used for coating paper or board. Since several detectors are used in the measurement, the equipment used is complicated and expensive. Another disadvantage of using several detectors is that the measurements are inaccurate, which is due to nonidealities in the optical path used by the detectors, which means that each detector sees the optics in a different manner. In addition, the strength of the signal to be detected weakens in proportion to the amount of components or detectors.

Another prior art solution to measure a coating is described in U.S. Pat. No. 5,338,361, which is incorporated herein by reference. In the solution according to the publication, components of two different coatings on the substrate are measured by using three separate NIR wavelength bands, the first wavelength band being sensitive to the first component, the second wavelength band to the second component and the third wavelength band to the substrate. In order to measure several different coatings more wavelength bands are used. Since this solution, too, employs several detectors in the measurement, the equipment used is complicated and expensive. A further disadvantage of using several detectors is that the measurements are inaccurate, which is due to nonidealities in the optical path used by the detectors, which means that each detector sees the optics in a different manner.

BRIEF SUMMARY OF THE INVENTION

It is an object of the invention to implement an improved method and an apparatus implementing the method. This is achieved by a method for measuring a coating from paper or board by means of IR radiation, the coating comprising at least two components. The method further comprises the steps of carrying out the measurement by one detector; measuring at least one component from the coating by using MIR radiation and at least one component by using NIR radiation, and, in order to measure at least one component by using MIR radiation: directing IR radiation at the coating; chopping the IR radiation directed at the coating; bandpass filtering a MIR wavelength band of the component, which is sensitive to the absorption of said at least one component from the IR radiation emerging from the coating; measuring the strength of the MIR radiation sensitive to the absorption; bandpass filtering a MIR wavelength band of the component, which is insensitive to the absorption of the component from the IR radiation emerging from the coating; measuring the strength of the MIR radiation insensitive to the absorption; measuring the strength of the absorption of the component by comparing the strength of the MIR radiation sensitive to the absorption and the strength of the MIR radiation insensitive to the absorption with each other; determining the amount of at least one component of the coating on the basis of the measured strength of at least one MIR absorption; and, in order to measure at least one component by using NIR radiation: bandpass filtering a NIR wavelength band of the component, which is sensitive to the absorption of the component from the IR radiation emerging from the coating; measuring the strength of the NIR radiation sensitive to the absorption; bandpass filtering a NIR wavelength band of the component, which is insensitive to the absorption of the component from the IR radiation emerging from the coating; measuring the strength of the NIR radiation insensitive to the absorption; measuring the strength of the absorption of the component by comparing the strength of the NIR radiation sensitive to the absorption and the strength of the NIR radiation insensitive to the absorption with each other; determining the amount of at least one component of the coating on the basis of the measured strength of at least one NIR absorption.

The invention also relates to a method for measuring a coating from paper or board by means of IR radiation. The method further comprises the steps of simultaneously measuring from the coating at least one component by using MIR radiation and at least one component by using NIR radiation, and, in order to measure at least one component by using MIR radiation: directing IR radiation at the coating; chopping the IR radiation directed at the coating; bandpass filtering a MIR wavelength band of the component, which is sensitive to the absorption of said at least one component from the IR radiation emerging from the coating; measuring the strength of the MIR radiation sensitive to the absorption; bandpass filtering a MIR wavelength band of the component, which is insensitive to the absorption of the component from the IR radiation emerging from the coating; measuring the strength of the MIR radiation insensitive to the absorption; measuring the strength of the absorption of the component by comparing the strength of the MIR radiation sensitive to the absorption and the strength of the MIR radiation insensitive to the absorption with each other;

determining the amount of at least one component of the coating on the basis of the measured strength of at least one MIR absorption; and, in order to measure at least one component by using NIR radiation: bandpass filtering a NIR wavelength band of the component, which is sensitive to the absorption of the component from the IR radiation emerging from the coating; measuring the strength of the NIR radiation sensitive to the absorption; bandpass filtering a NIR wavelength band of the component, which is insensitive to the absorption of the component from the IR radiation emerging from the coating; measuring the strength of the NIR radiation insensitive to the absorption; measuring the strength of the absorption of the component by comparing the strength of the NIR radiation sensitive to the absorption and the strength of the NIR radiation insensitive to the absorption with each other; determining the amount of at least one component of the coating on the basis of the measured strength of at least one NIR absorption.

The invention further relates to an apparatus for measuring a coating from paper or board by means of IR radiation, the coating comprising at least two components. The apparatus further comprises one detector for measuring at least one component from the coating by using MIR radiation and at least one component by using NIR radiation, the apparatus comprising: an optical power source for radiating IR radiation to the coating; a chopper for chopping the IR radiation directed at the coating; and, in order to perform MIR measurement for one component the apparatus comprises: a bandpass filter for filtering a MIR wavelength band of the component, which is sensitive to the absorption of the component from the IR radiation emerging from the coating; a detector is arranged to detect MIR radiation sensitive to the absorption and to convert the strength of the detected MIR radiation into an electrical signal of equal strength, by means of which signal the apparatus is arranged to measure the strength of the MIR radiation sensitive to the absorption; a bandpass filter for filtering a MIR wavelength band of the component, which is insensitive to the absorption of the component from the IR radiation emerging from the coating; the detector is arranged to detect MIR radiation insensitive to the absorption and to convert the strength of the detected MIR radiation into an electrical signal of equal strength, by means of which signal the apparatus is arranged to measure the strength of the MIR radiation insensitive to the absorption; the apparatus is arranged to measure the strength of the absorption of the component by comparing the strength of the MIR radiation sensitive to the absorption and the strength of the MIR radiation insensitive to the absorption with each other; the apparatus is arranged to determine the amount of at least one component of the coating on the basis of the measured strength of at least one MIR absorption; and, in order to perform NIR measurement for one component the apparatus comprises: a bandpass filter for filtering a wavelength band of at least one other component, which is sensitive to the absorption of said at least one other component in the NIR region from the IR radiation emerging from the coating; the detector is arranged to detect NIR radiation sensitive to the absorption and to convert the strength of the detected NIR radiation into an electrical signal of equal strength, by means of which signal the apparatus is arranged to measure the strength of the NIR radiation sensitive to the absorption; a bandpass filter for filtering a wavelength band of at least one other component, which is insensitive to the absorption of said at least one other component in the NIR region from the IR radiation emerging from the coating; the detector is arranged to detect NIR radiation insensitive to the absorption and convert the strength of the detected NIR radiation into an electrical signal of equal strength, by means of which signal the apparatus is arranged to measure the strength of the NIR radiation insensitive to the absorption; the apparatus is arranged to measure the strength of the absorption of the component by comparing the strength of the NIR radiation sensitive to the absorption and the strength of the NIR radiation insensitive to the absorption with each other; the apparatus is arranged to determine the amount of at least one component of the coating on the basis of the measured strength of at least one NIR absorption.

The invention further relates to an apparatus for measuring a coating from paper or board by means of IR radiation, the coating comprising at least two components. In addition, the apparatus is arranged to simultaneously measure at least one component from the coating by using MIR radiation and at least one component by using NIR radiation, the apparatus comprising: an optical power source for radiating IR radiation to the coating; a chopper for chopping the IR radiation directed at the coating; and, in order to perform MIR measurement for one component the apparatus comprises: a bandpass filter for filtering a MIR wavelength band of the component, which is sensitive to the absorption of the component from the IR radiation emerging from the coating; a first detector for detecting MIR radiation sensitive to the absorption and converting the strength of the detected MIR radiation into an electrical signal of equal strength, by means of which signal the apparatus is arranged to measure the strength of the MIR radiation sensitive to the absorption; a bandpass filter for filtering a MIR wavelength band of the component, which is insensitive to the absorption of the component from the IR radiation emerging from the coating; the first detector is arranged to detect MIR radiation insensitive to the absorption and to convert the strength of the detected MIR radiation into an electrical signal of equal strength, by means of which signal the apparatus is arranged to measure the strength of the MIR radiation insensitive to the absorption; the apparatus is arranged to measure the strength of the absorption of the component by comparing the strength of the MIR radiation sensitive to the absorption and the strength of the MIR radiation insensitive to the absorption with each other; the apparatus is arranged to determine the amount of at least one component of the coating on the basis of the measured strength of at least one MIR absorption; and, in order to perform NIR measurement for one component the apparatus comprises: a bandpass filter for filtering a wavelength band of at least one other component, which is sensitive to the absorption of said at least one other component in the NIR region from the IR radiation emerging from the coating; a second detector for detecting NIR radiation sensitive to the absorption and converting the strength of the detected NIR radiation into an electrical signal of equal strength, by means of which signal the apparatus is arranged to measure the strength of the NIR radiation sensitive to the absorption; a bandpass filter for filtering a wavelength band of at least one other component, which is insensitive to the absorption of said at least one other component in the NIR region from the IR radiation emerging from the coating; the second detector is arranged to detect NIR radiation insensitive to the absorption and convert the strength of the detected NIR radiation into an electrical signal of equal strength, by means of which signal the apparatus is arranged to measure the strength of the NIR radiation insensitive to the absorption; the apparatus is arranged to measure the strength of the absorption of the component by comparing the strength of the NIR radiation sensitive to the absorption and the strength of the NIR radiation insensitive to the absorption with each other; the apparatus is arranged to determine the amount of at least one component of the coating on the basis of the measured strength of at least NIR absorption.

The preferred embodiments of the invention are disclosed in the dependent claims.

The method and system of the invention provide a plurality of advantages. As the amount of components to be detected increases, the amount of detectors does not. Furthermore, the strength of the radiation to be detected does not decrease in proportion to the amount of components to be detected or to the amount of detectors. Interferences, for their part, are efficiently eliminated by combining radiation chopping and filtering.

BRIEF DESCRIPTION OF THE SEVERAL VIEWS OF THE DRAWINGS

In the following the invention will be described in greater detail by means of preferred embodiments and with reference to the attached drawings, in which.

DETAILED DESCRIPTION OF THE INVENTION

The solution according to the invention is particularly applicable to measuring coating components of paper or board and measuring moisture of paper and board.

In this application, the NIR (Near IR) region of IR (InfraRed) radiation refers to an electromagnetic spectrum band of 700 nm to 2500 nm. The MIR (Middle IR) region, for its part, refers to an electromagnetic spectrum band of 2500 nm to 20000 nm. These definitions correspond to the understanding of a person skilled in the art on NIR and MIR radiation.

In the inventive solution, one or more coating components, such as calcium carbonate, kaolin, silicon and water, are measured by using MIR radiation, and one or more components, such as kaolin, talc, gypsum, latex, starch, silicon and water, are measured by using NIR radiation. In the method, the moisture content is determined by measuring water.

Figure 1A:
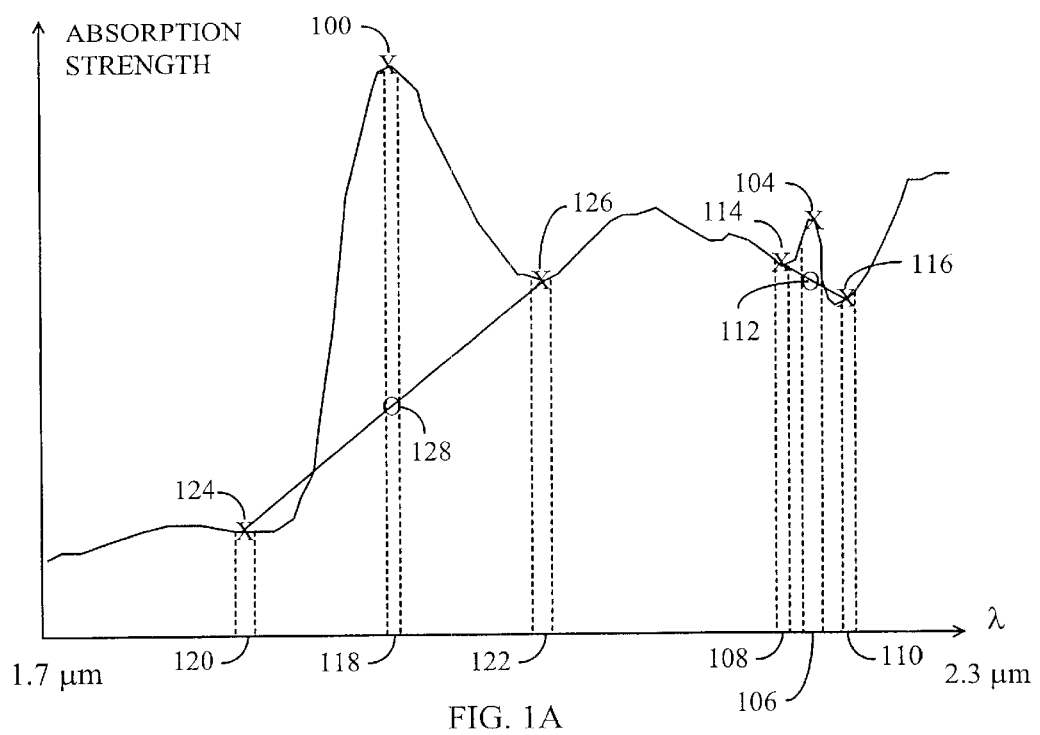
FIG. 1A shows NIR radiation absorption of different components.
Figure 1B:
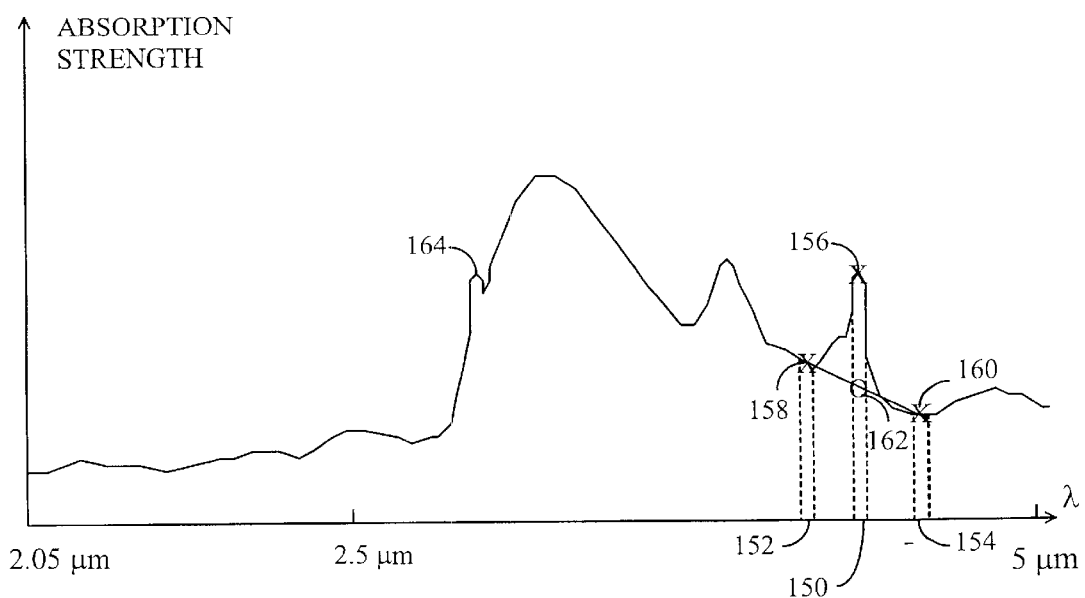
FIG. 1B shows MIR radiation absorption of different components.

To begin with, let us examine the background of FIGS. 1A and 1B. Absorption means the attenuation of radiation strength, which is measured by intensity, in a material to be measured. When the intensity $I_0$ of optical radiation propagates through an absorbing material, the radiation attenuates according to Bouguer law in the following manner:

$$I = I_0 \cdot e^{-\alpha x},$$

where $I_0$ is radiation intensity arriving at a material, x is the distance traveled by the radiation, I is the radiation intensity after the traveled distance x, $\alpha$ is the absorption coefficient and e is the base number of the natural logarithm. The amount of absorption as such is the product ($\alpha x$) of the absorption coefficient and the distance traveled by the radiation. As the detector can directly measure only the strength of radiation, the strength of absorption is formed in a manner known per se by, for example, directly comparing the intensity $I_0$ directed to an object to be measured or the reference intensity in known proportion to it, and the intensity I measured by the detector:

$$\alpha x = -\log_e \frac{I}{I_0}.$$

Let us now take a closer look at the absorbency of paper and board coatings as a function of wavelength by means of FIGS. 1A and 1B. In FIGS. 1A and 1B, the x-axis is the wavelength and the y-axis is the absorption strength. FIG. 1A shows an absorption curve of board coated with kaolin in the NIR region. An absorption peak 100 at 1940 nm is caused by water, an absorption peak 102 at 2100 nm is caused by cellulose and an absorption peak 104 at 2208 nm is caused by kaolin. In the inventive solution the absorption strength of kaolin can be measured by NIR radiation at a wavelength band, the middle wavelength of which is at the point sensitive to absorption, i.e. at the maximum absorption point at a wavelength of about 2208 nm. During the measurement, the object to be measured is illuminated with IR radiation, and the radiation strength 104 of the wavelength band 106 is measured. To determine the strength of the absorption peak 104 caused by kaolin, the radiation strength is also measured at other points 108, 110 which are not sensitive to absorption. This measurement is performed at least from one side of point 106 sensitive to absorption, i.e. from point 108 or 110, the middle wavelengths of which can be freely positioned in the NIR region. However, it is preferable to carry out the measurement from both sides of point 104 sensitive to absorption (points 114 and 116).

When measurements are performed from both sides of the point where the component is sensitive to absorption, an estimate 112 of the radiation strength level outside the absorption peak can be formed. The estimate is formed by interpolating the radiation strength at measuring points 108 and 110. There may be more than two measuring points outside the wavelength region 106 sensitive to absorption. Thus, the estimate 112 is insensitive to the absorption of the component, and it takes into account a possible change of the baseline in different measurements (the baseline corresponds to the line segment combining points 114, 112 and 116 in FIG. 1A). Also an estimate 128 is insensitive to the absorption of the component and takes into account a possible change of the baseline (this baseline corresponding to the line segment which combines points 124, 126 and 128).

When the radiation strength at point 106 sensitive to the kaolin absorption is compared with at least one radiation strength measured at a point that is not sensitive to absorption, the absorption strength of kaolin can be determined, for instance, as the difference of the radiation strengths at points 104 and 114 (or at points 104 and 116). Instead of the difference, the quotient or other similar mathematical operation can be employed. The most accurate measurement concerning the absorption strength at the wavelength band 106 is obtained when the difference is formed between the absorption peak 104 and the estimate 112.

Correspondingly, also the strength of the absorption caused by water at a wavelength band 118 having a middle wavelength of about 1940 nm can be measured by means of NIR radiation. In this case, the radiation strength 100 of the wavelength band 118 is compared with the radiation strength 124, 126 of the water absorption, which is measured at the insensitive wavelength band 120, 122. By measuring the amount of water, i.e. the moisture content, the measurement of the amount of other components can be specified.

FIG. 1B shows absorption curves of paper in the MIR region. In the MIR region, the absorption strength of calcium carbonate can be measured similarly as the absorption strength of kaolin and water was measured in FIG. 1A. The radiation strength 156 of calcium carbonate is measured by means of MIR radiation at a wavelength band 150 with a middle wavelength of about 3950 nm. In this measurement, too, the radiation strength is also measured outside the wavelength band 150 sensitive to the calcium carbonate absorption, at points 158 and/or 160, for instance. Furthermore, it is preferable to form the mean value 162 for the radiation strengths formed at the wavelength bands 152 and 154 and compare the radiation strength 156 with the mean value 162 in order to measure the absorption strength. The absorption strength of kaolin at a wavelength band 164 with a middle wavelength of about 2700 nm can also be measured by means of MIR radiation.

Let us now take a closer look at the method according to the invention, wherein the measurement is carried out by one detector. The measurement employs both MIR and NIR radiation, which are measured at different times. An MCT (Mercury Cadmium Telluride) detector or the like is used as a detector. The type of the detector is, however, not essential for the invention, but the essential matter is that the detector is capable of detecting the radiation to be measured. At least one component is measured from a paper or board coating by means of MIR radiation, and at least one component is measured from the coating by means of NIR radiation. To carry out the measurement in the method, IR radiation from the optical power source, chopped by means of a chopper into light pulses, is directed at the coating. In order to perform the detection, radiation emerging from the coating is bandpass filtered and usually also chopped synchronously with the IR radiation illuminating the coating. The IR radiation emerging from the coating comprises pulsed optical radiation from the optical power source and optical radiation emitted by the coating itself. Detection is performed in the measurement direction, which is other than the direction of specular reflection.

Let us now examine measurement carried out by using MIR radiation. At least one wavelength band of at least one component, the band being sensitive to the absorption of said at least one component in the MIR region, is bandpass filtered from the chopped optical radiation, and the strength of the MIR radiation sensitive to absorption is measured. The point of MIR radiation sensitive to absorption is the maximum absorption point of this component. In case of calcium carbonate, the absorption occurs at an optical band with a middle wavelength of about 3950 nm. In case of kaolin, the middle wavelength of absorption is about 2700 nm. An interference filter is used as a bandpass filter. Next, at least one absorption strength in proximity of the maximum absorption is measured in order to find out how strong the maximum absorption is compared to its environment. This is done in the following manner. A wavelength band of said at least one component, the band being insensitive to the absorption of said component in the MIR region, is bandpass filtered from the chopped IR radiation, and the strength of the MIR radiation insensitive to absorption is measured. Thereafter, the absorption strength of one or more components is determined by comparing, for each component specifically, the strength of the MIR radiation sensitive to absorption and the strength of the MIR radiation insensitive to absorption with each other. Finally, the amount of at least one component of the coating is determined in the MIR measurement on the basis of the strength of the MIR absorption.

Let us now examine more closely the measurement in the NIR region, which is similar to the measurement in the MIR region. A wavelength band of at least one other component, the band being sensitive to the absorption of said at least one other component in the NIR region, is bandpass filtered from the chopped IR radiation, and the strength of the NIR radiation sensitive to absorption is measured. The other material can be, for instance, kaolin, water, talc, gypsum, latex, starch, silicon or a special coating, such as temperature-sensitive ink. To measure the absorption strength, absorption is also measured at a reference wavelength, which is other than the wavelength band causing the maximum absorption. In this case, a wavelength band of said at least one other component, the band being insensitive to the absorption of said at least one other component in the NIR region, is bandpass filtered from the chopped IR radiation, and the strength of the NIR radiation insensitive to absorption is measured. Thereafter, the absorption strength of said one or more other components is measured by comparing, for each component specifically, the strength of the NIR radiation sensitive to absorption and the strength of the NIR radiation insensitive to absorption with each other. Finally, the amount of said at least one other component of the coating is determined on the basis of the strength of the NIR absorption.

When two detectors are used, the one of which measures MIR radiation and the other one NIR radiation, the measurement is otherwise similar, but both the MIR and the NIR measurement are performed simultaneously. NIR radiation can be detected with an InGaAs (Indium Gallium Arsenide) detector, for example. The type of the detector is, however, not essential for the invention; the most important thing is that the detector is capable of detecting the radiation to be measured.

Figures 2A, 2B:
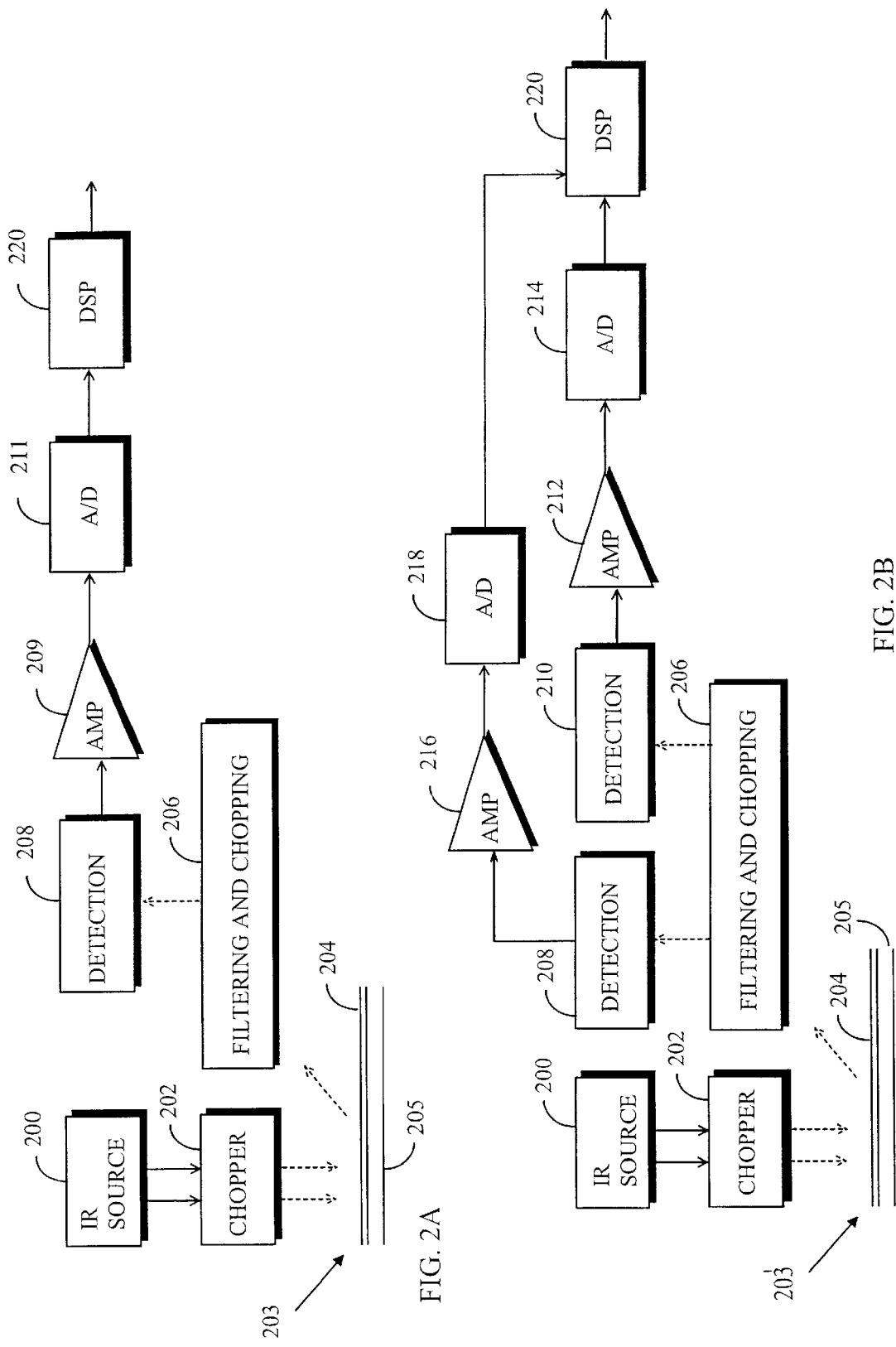
FIG. 2A is a block diagram of an apparatus when one detector is used.
FIG. 2B is a block diagram of an apparatus when two detectors are used.

Let us now examine the solution of the invention by means of FIG. 2A which is a simplified block diagram of an inventive measuring apparatus. In the inventive solution, an optical radiation source 200 operating in at least the IR region transmits optical radiation through a chopper 202 to an object to be measured 205. The object of measurement 205 is of paper or board, the coating 204 of which will be measured. If uncoated paper or board is measured, the inventive solution does not naturally detect a sufficient amount of coating component for the measurement. However, paper may contain, for example, calcium carbonate as a filler, which can be observed in the measurement. When measuring coatings, the inventive solution measures the amount of the coating component.

The chopper 202 allows optical radiation to momentarily pass through it, and part of the time the chopper 202 prevents optical radiation from penetrating it. What is essential in the operation of the chopper 202 is that during the illumination time, the object of measurement 205 is illuminated by IR radiation emitted by the optical power source 200 and during the off-period of illumination the object of measurement is not illuminated by IR radiation emitted by the optical power source 200. This way, the chopper 202 chops the optical radiation into light pulses, which hit an object to be measured 204.

From the object of measurement 204, the optical radiation is reflected and scattered into different directions. Part of the optical radiation is directed towards block 206 where the optical radiation is bandpass filtered for the detection. At the same time, the optical radiation is usually also chopped. In the inventive solution, however, the optical radiation reflected from the object of measurement 204 is not measured from the direction of specular reflection. In block 206, filtering is performed separately with MIR and NIR filters, which are preferably interference filters. When the strength of MIR radiation is measured, the radiation from the object of measurement 204 is filtered with the MIR filter. When the strength of NIR radiation is measured, the radiation from the object of measurement 204 is filtered with the NIR filter. The detection time is the time when MIR or NIR radiation is allowed to pass to a detector 208 for measurement. The detection is performed synchronously at the same time as the object of measurement is illuminated with optical radiation. In addition, when the object of measurement 204 is not illuminated with IR radiation during the off-period of detection, radiation emerging from the coating is mainly prevented from passing to the detector 208 for the measurement.

Figure 5:
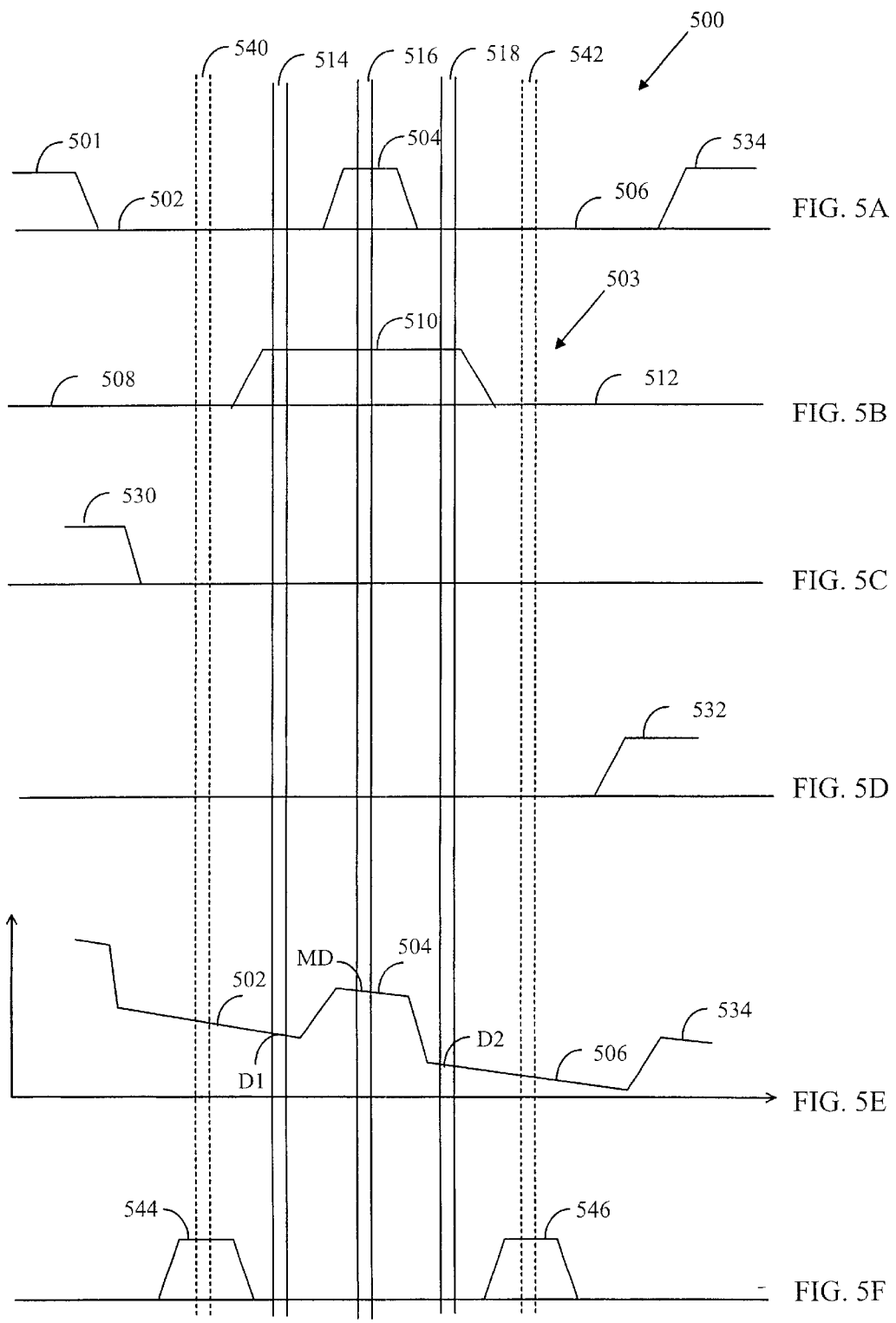
FIGS. 5A to 5F illustrate the timing of optical rays chopped with a chopper.

When a paper web, which is the object of measurement, is not illuminated by IR radiation, radiation emitted from the paper web is measured in order to detect and eliminate interferences affecting the measurement. The inventive solution also utilizes measurement of paper web temperature, carried out by means of IR radiation emerging from the paper web itself, when the paper web to be measured is not illuminated. In the temperature detection, the same detector as in the coating measurement is used. The timing of the illumination and detection is explained in greater detail in connection with FIG. 5.

During the coating measurement, the detector thus detects the filtered IR radiation and in the temperature measurement, it detects the filtered or not filtered radiation and converts the strength of the detected filtered IR radiation into an electrical signal of equal strength. This electrical signal is amplified in a preamplifier 209 and converted into digital in an A/D converter 211. On the basis of the digital signal, a digital signal processing block 220 measures the strength of the detected IR radiation, calculates the amount of coating and determines the temperature of the paper web. When the temperature is determined, the principle of black-body radiation known per se is applied, which means that the power of the radiation entering the detector is in relation to the temperature.

In coating and temperature measurements according to the inventive solution, MIR and NIR measurements can be performed at different time instances by means of one detector 208, from which a measurement signal converted into electrical form propagates to the preamplifier 209, A/D converter 211 and finally to digital signal processing in block 220.

Let us now examine the solution of the invention by means of FIG. 2B. The solution is in many respects similar to the solution of FIG. 2A, but now two detectors 208 and 210 are used. Optical radiation passing to the detector 208 is filtered in block 206 in such a way that only NIR radiation is allowed to pass to the detector 208 while only MIR radiation is allowed to pass to the detector 210. The measurement signal of both detectors is amplified in preamplifiers 212 and 216, and the electrical measurement signals are converted into digital in A/D converters 214 and 218. The digital signals are processed in the same way as in the signal processing block 220 in connection with FIG. 2A.

Figure 3A:
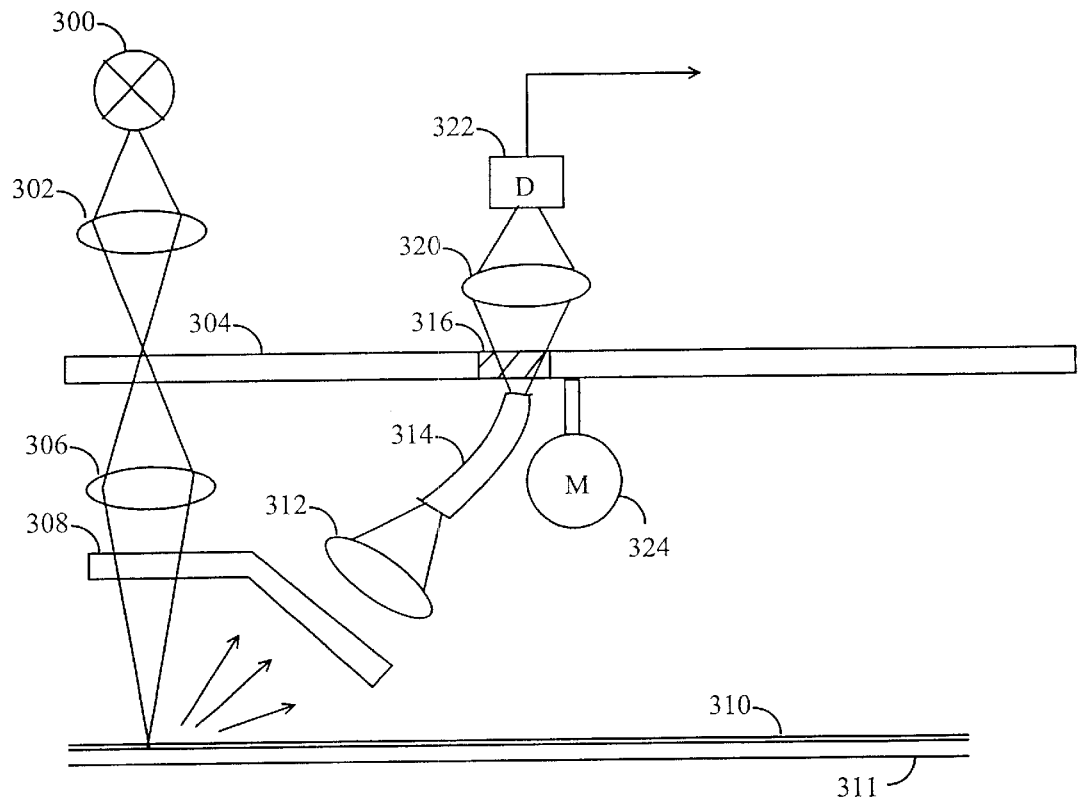
FIG. 3A is a structural view of the apparatus when one detector is used.
Figure 3B:
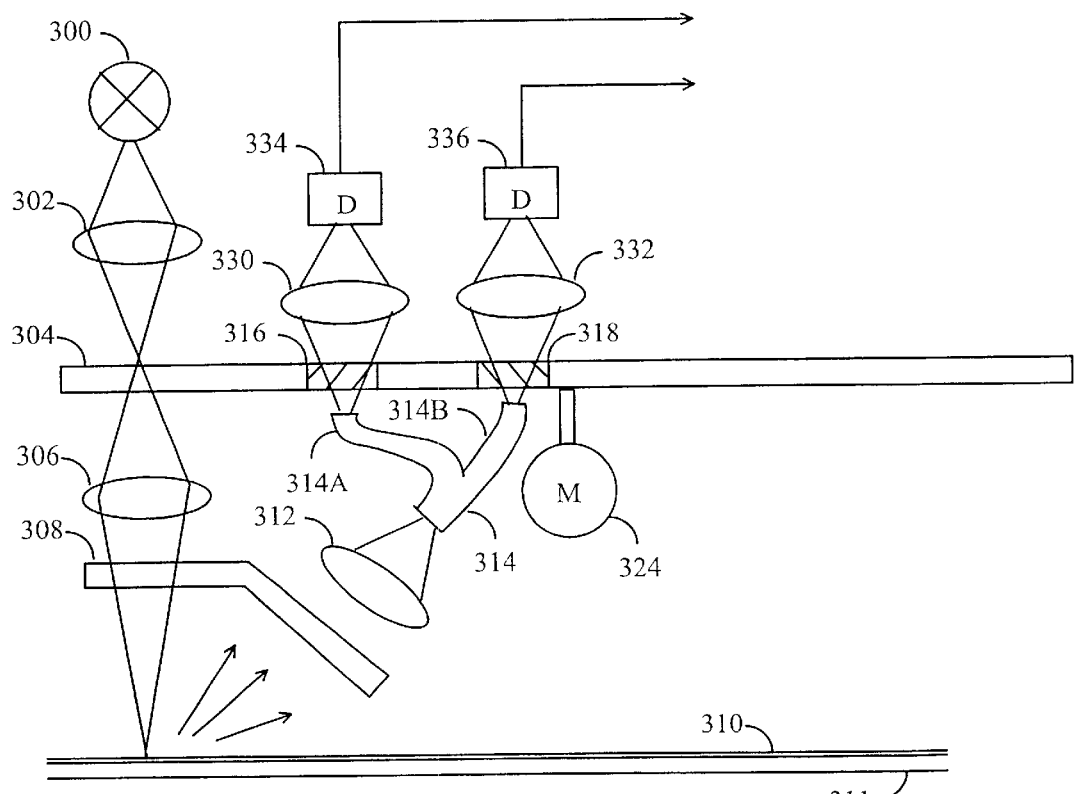
FIG. 3B is a structural view of the apparatus when two detectors are used.

Let us now observe by means of FIGS. 3A and 3B how the apparatus of the inventive solution is implemented. An optical power source 300 radiates optical power to a lens 302. The lens 302 makes an image of the optical power source 300 to a chopper 304. Instead of the lens 302, a lens combination or a concave mirror can be used, which makes an image of the optical power source 300 to the chopper 304. After the chopper 304, an image of the lens 302 making an image of the optical power source 300 to the chopper is made by a lens 306 to an object of measurement 311, which is of paper or board and comprises a coating 310. In this case, too, a lens combination or a concave mirror can be used instead of the lens 306. This illumination solution is called Köhler illumination and it provides the object of measurement 310 with even diffuse illumination. The illumination manner as such is not essential for the inventive solution, but it is sufficient that the surface to be measured is illuminated by IR radiation. A protective means 308, which is made of plastic, glass or some other material that passes through IR radiation to be measured, can be used between the lens 306 and the object of measurement 310. Particularly under industrial conditions, the protective means 308 protects imaging optics (lenses 302 and 306), the chopper 304 and the optical power source 300 from impurities.

Optical radiation which is reflected and scattered from the object of measurement 310 is collected by a lens 312 and focused on an optical fiber or fiber bundle 314. Between the object of measurement 310 and the lens 312 there is preferably a protective means 308, which, particularly under industrial conditions, also protects the receiver of optical radiation from impurities. From the fiber or fiber bundle 314 the optical radiation is transferred towards the filtering. The fiber or fiber bundle 314 is not necessarily required, since the optical radiation can be directly focused through the filter on the detector. By using the optical fiber or fiber bundle it is possible to position the object to be detected far from the object of measurement, in proximity of which impurities and high temperature could cause problems. In FIG. 3A, which corresponds to the solution of FIG. 2A, only one detector 322 is used in the measurement. One detector 322 can detect only MIR radiation or NIR radiation at a time, but not MIR radiation and NIR radiation simultaneously. Therefore, the optical radiation from the fiber 314 is filtered with a MIR filter 316 and a NIR filter 318 at different times. The filtered IR radiation is focused by a lens 320 on the detector 322. Lenses can be, for example, binary lenses, diffractive lenses or refractive lenses. The chopper 304 is preferably a rotary disc provided with teeth and a filter and illustrated in FIG. 4 in greater detail. The rotary disc is rotated by a motor 324.

In FIG. 3B, the transmitting part of optical radiation is similar to that of FIG. 3A, but the receiving part which receives the optical radiation from the object of measurement 310 is slightly different. Between the object of measurement 310 and the lens 312 there is preferably a protective means 308, which, particularly under industrial conditions, protects also the receiver from impurities. The lens 312 focuses the radiation emerging from the object of measurement 310 on the optical fiber bundle 314. Since two detectors 334 and 336 can be used in this inventive solution, the optical fiber bundle 314 divides into two branches 314A and 314B. The optical radiation from the branch 314A is filtered by the MIR filter 316 and the radiation from the branch 314B is simultaneously filtered by the NIR filter 318. The filtered MIR radiation is focused by a lens 330 on the detector 334, and the filtered NIR radiation is focused by a lens 332 on the detector 336. Also in this case, the chopper 304 is preferably a rotary disc, which is described in greater detail in FIG. 4. The disc is rotated by the motor 324. Instead of a rotary disc, optical switches known per se, such as mechanical, electro-optical, magneto-optical and acousto-optical switches, can be used for chopping optical radiation. The operation of the switches is timed as presented in FIGS. 5A to 5F.

Figure 4:
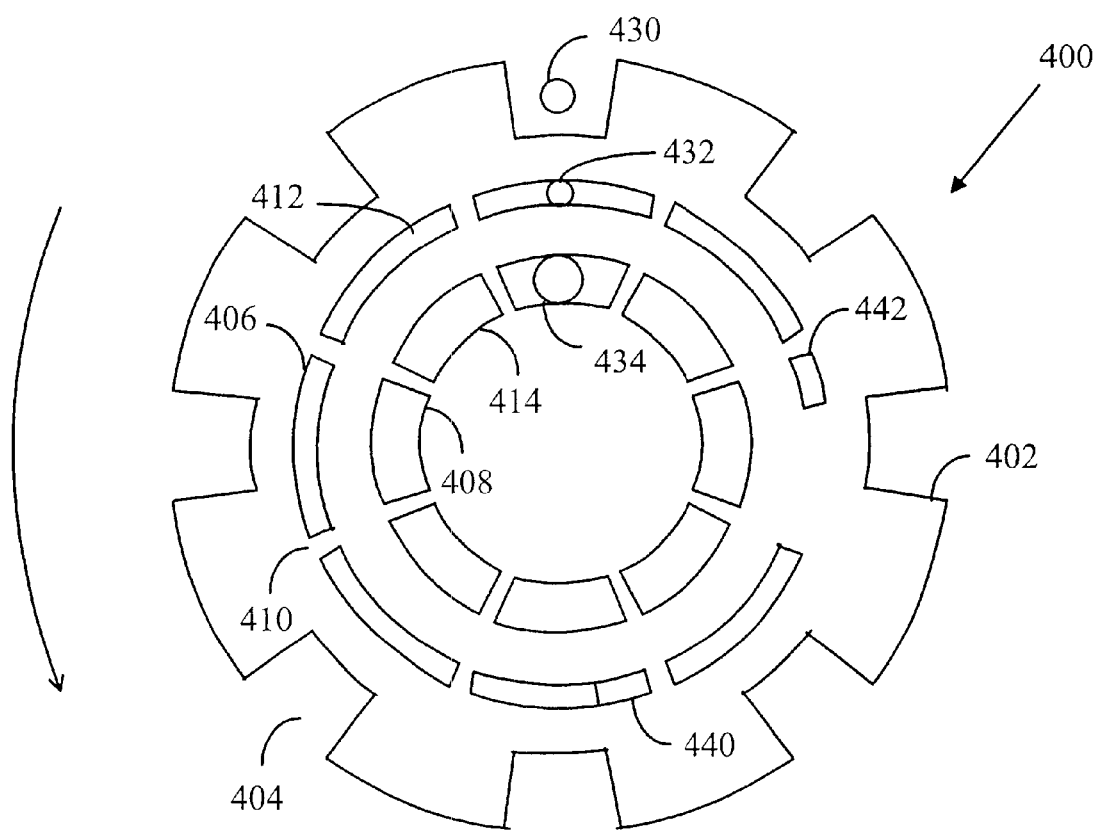
FIG. 4 shows a chopper disc.

Let us now take a closer look at the chopper used in the inventive solution by means of FIG. 4. A chopper 400 is preferably a disc-like optical radiation chopper comprising teeth 402 for preventing IR radiation from passing from the optical power source to the surface to be measured, and teeth gaps 404 for allowing IR radiation to pass from the optical power source to the surface to be measured. The disc-like chopper 400 also comprises at least two MIR filters 406, 412 operating as bandpass filters correspondingly allowing MIR radiation to pass to the detector at least at two separate bands. The MIR filters 406, 412 are positioned circumferentially in the disc-like chopper 400. The maximum absorption point is measured at one bandpass MIR filter and a point outside the maximum absorption point is measured at the remaining one or more bands. Likewise, the chopper 400 comprises at least two NIR filters 408, 414 operating as bandpass filters and passing NIR radiation to the detector at two separate bands. The NIR filters 408, 414 are positioned circumferentially in the disc-like chopper 400. In this case, too, the optical band of one filter passes NIR radiation to the detector at the maximum absorption point of the measured coating component. One or more other NIR filters pass NIR radiation to the detector at bands other than that of the maximum absorption point.

In addition, the disc-like chopper 400 comprises filter gaps 410 preventing IR radiation from propagating to the detectors. The filters 406, 408 are positioned such that when optical radiation 430 passes through the teeth 402 gaps 404 at the outer edge of the chopper 400 towards the object of measurement, the filters 406 and 408 simultaneously pass IR radiation 432 and 434 reflected and filtered from the paper web to the detectors.

The chopper disc 400 is preferably rotated by an electric motor, and when the disc rotates, the teeth and filter gaps chop the radiation passing to the detector(s) and the surface to be measured. When only one detector is used, as in FIGS. 2A and 3A, MIR and NIR filters are positioned one after the other on the circumference of the disc-like chopper 400, and they filter MIR and NIR radiation alternately to one detector for the measurement (this is not shown in the figure, as it is obvious to a person skilled in the art). In the inventive solution, the middle wavelength of the bandpass of the MIR and NIR filters can be adjusted by changing the angle of inclination of the filters with respect to the direction of IR radiation penetrating the filters. An advantage of such a measuring arrangement is that increasing the number of MIR and NIR bands to be measured does not make the apparatus much more complicated, and optical power, which is used in the measurement, is typically not increased.

To measure the temperature of the paper web, IR radiation radiated by the paper web is passed through the filter to the detector at time instant 440. The measuring can also be performed such that one or more filters are replaced by an opening 442 in the chopper 400, which allows radiation to pass to the detector when no IR radiation is directed at the paper web. Thus, the detector can receive IR radiation from the paper web at its entire response band. It is advantageous to use a detector detecting MIR radiation for the temperature measurement. It is also possible to measure the temperature when one teeth 404 gap is covered and no IR radiation can pass from the optical radiation source to the paper web.

Let us now examine illumination and detection of an object of measurement by means of FIGS. 5A to 5F. The y-axis represents penetration on a free scale, the x-axis represents time T, and all curves are on the same time axis. In FIG. 5A, a curve 500 illustrates the penetration of a chopper between an optical power source and an object of measurement as a function of time. A curve 503 of FIG. 5B illustrates the penetration of a chopper between an object of measurement and a detector as a function of time at a first wavelength to be measured. The chopper comprises optical filters and possibly also openings for passing optical radiation to the surface to be measured and for detection. In the beginning of the process, the chopper passes optical radiation to the surface to be measured and the detector (curve 530 in FIG. 5C and 501 in FIG. 5A). The curve 530 refers to measurement at a second wavelength to be measured. The measurement at different wavelengths is performed in the same manner.

Since in FIGS. 5A to 5F the surface measurement has already been performed at the second wavelength to be measured, the surface measurement at the first wavelength is described in greater detail by means of FIGS. 5A and 5B. First, the chopper prevents the first radiation used in the measurement from passing to the surface to be measured and the detector (curve points 502 and 508). In the inventive solution, the chopper between the object of measurement and the detector preferably starts passing IR radiation to the detector at the first wavelength to be measured (penetration at point 510) a little before the chopper between the optical power source and the object of measurement starts passing optical radiation to the surface to be measured (penetration at point 504). Interference level is then measured at time instant 514 for the first time. When also the chopper between the optical power source and the object of measurement starts passing optical radiation to the object of measurement (curve point 504), the total IR radiation strength of the object's first wavelength to be measured can be measured at time instant 516. In the inventive solution, the interference level is measured at the first wavelength to be measured for the second time when the chopper between the optical power source and the object of measurement prevents optical radiation from passing to the object of measurement at time instant 518. The chopper no longer passes the first radiation to be measured to the detector at curve point 512.

The measurement at a third wavelength can be started when the chopper starts passing radiation to the detector in accordance with the curve 532 of FIG. 5D. Before that, however, the interference level can be measured when the chopper prevents the first radiation used in the measurement from passing to the surface to be measured and the detector at point 506. The interference level can be measured again, or the measurement can be utilized at point 518. Finally at point 534, the chopper also passes radiation to the surface to be measured (measuring point is not shown in FIG. 5D). In this way, several components of the coating can be preferably measured at many wavelengths.

FIG. 5E illustrates interference level measurement in greater detail. The measurement is similar to that of FIG. 5A, but, due to interferences, the baseline of the measured radiation strength is slanting. In the inventive solution the first interference level D1 is measured at time instant 514. Thus, interferences from the detector, protective means (shown by a reference number 308 in FIGS. 3A and 3B), object of measurement and electronical and optical operation of the apparatus in general can be measured. For instance, the temperature of the paper web to be coated is usually fairly high (about 100° C., for instance) and therefore the paper web radiates a significant amount in the MIR and NIR regions. When also the chopper between the optical power source and the object of measurement starts passing optical radiation to the object of measurement (curve point 504), the actual MD measurement of the total IR radiation strength of the object can be performed at time instant 516. In the inventive solution, yet another measurement of the interference level D2 is performed when the chopper between the optical power source and the object of measurement prevents optical radiation from passing to the object of measurement at time instant 518. The average interference level D is formed by adding the interference levels D1 and D2 together and dividing this by two, i.e. by utilizing the formula D=(D1+D2)/2. This provides the advantage that an average interference level D can be determined at the measuring instant 516 also when the interference level drifts. In the digital signal processing section, the measurement signal strength M free of interference is formed by the difference of the actual measurement signal MD and the interference level D, i.e. according to the formula M=MD−D. Other mathematical operations can be used in calculating interferences, too.

FIG. 5F illustrates the timing of the temperature measurement of a paper web according to the invention. The measurement is carried out when the paper web is not illuminated by pulsed optical radiation at instants 540 and 542. The measurement times can thus be anywhere between the light pulses. Radiation emerging from the paper web is passed to the detector at time intervals 544 and 546. The measurement can also be carried out when the source emitting optical radiation to the paper web is switched off. Hence, the temperature of the paper web can be measured each time when IR radiation radiating from the paper web is passed to the detector. By using the measured temperature, the temperature of the paper web can be adjusted and the drying process of the paper web and of the coated paper in particular can be optimized. In IR drying, IR radiation is directed from an IR radiation source at the paper web, the IR radiation increasing the temperature of the paper web. For example radiators heated by electricity or gas, i.e. IR dryers, can function as IR radiation sources.

The temperature of the paper web is preferably measured at several points in the transverse direction of the paper web in order to form a temperature profile of the paper web. The profile can be measured by means of one or more sensors such that the sensors are static or that the sensors traverse, i.e. move back and forth in the transverse direction of the paper web. The measuring arrangement thus comprises a desired number of sensors measuring the paper web, which are functionally connected to a measurement and control block. The measurement block preferably controls dryers. Dryers include blow dryers, steam-pressure cylinder dryers and IR dryers. The solution of the invention can control, optimize and monitor the condition of the dryers. In the coating process, the temperature of the coating paste can be prevented from increasing so high that the surface will solidify. If the surface temperature of the coating paste increases too much and the surface solidifies, the water inside the paste boils and explodes the surface. In addition, the temperature of the paper web can be measured at several locations in the machine direction of the web in order to form a temperature profile of the paper web in the machine direction. By optimizing the drying process, energy can be saved. The measuring arrangement of the paper web temperature keeps the temperature of the paper web constant both in the transverse direction and in the machine direction. As a result, paper shrinkage remains constant, which reduces folding and enables a high production rate.

When the temperature of the paper web is measured before and after the dryer, the measured temperature can be used for monitoring the condition of the dryer and for informing the operator of the paper machine of a potential defect.

Figure 6:
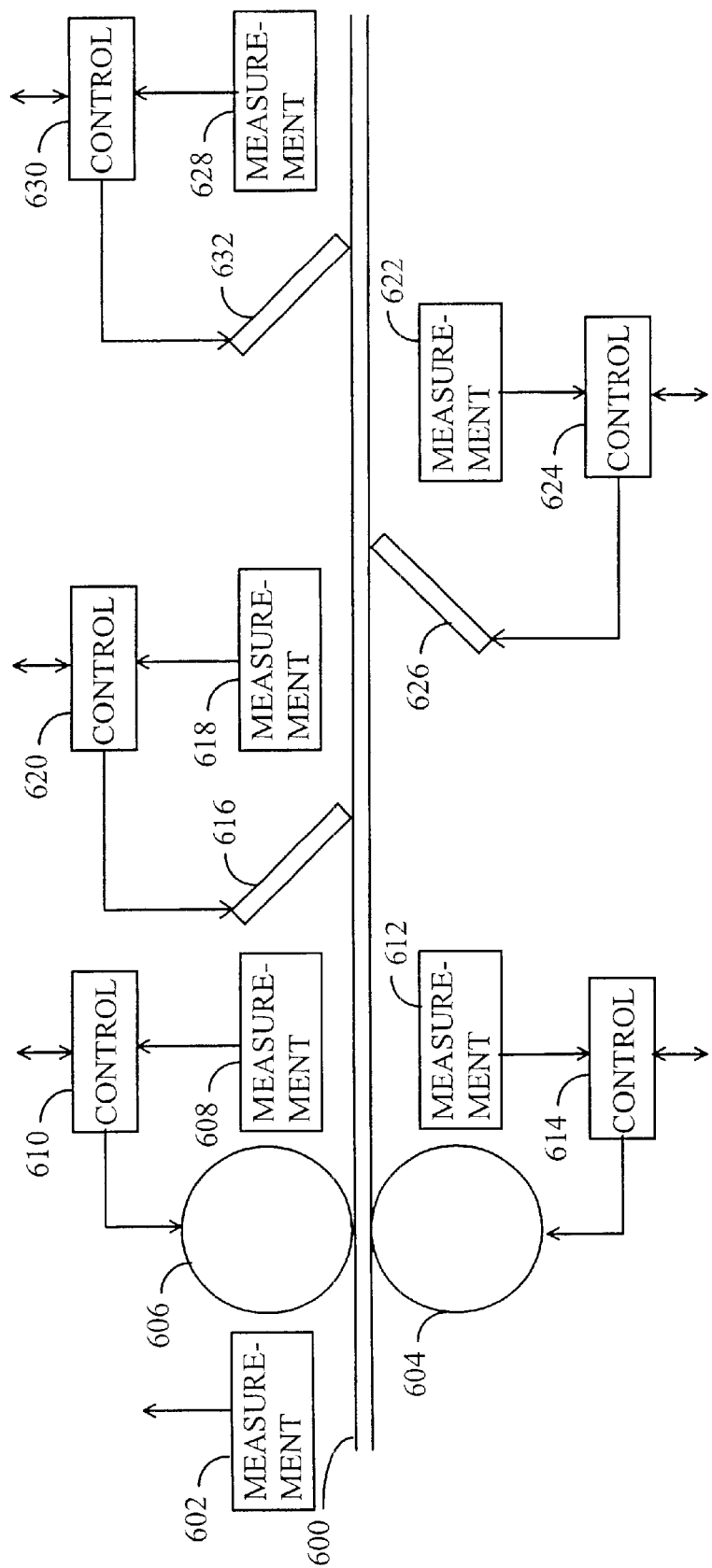
FIG. 6 shows how the apparatus can be applied to measuring coatings of a paper machine.

FIG. 6 illustrates a paper coating process of a paper machine. When paper or board is coated several times, the amount of coating of each coating layer can be measured by the inventive solution. As a paper web 600 travels towards the coating process, the amount of materials sensitive to measurement are measured from uncoated paper. Fillers, the most common of which are kaolin, talc and calcium carbonate, are added to paper pulp, for example. Paper is first coated on both sides in coating heads 604 and 606. The amount of a coating component or coating components is measured by measuring apparatuses 608 and 612 according to the inventive method. The measurement result is transferred from the measuring apparatus 608 to a controller 610, which controls the coating head 606 and aims at keeping the amount of coating at a desired level. The amount of coating can be increased or decreased depending on whether the measured amount of coating is big or small with respect to the desired level. The controller 610 is preferably connected to a computer (not shown in the figure) controlling the entire paper machine.

Similarly, a coating head 616 applies coating on paper from above, and the total amount of coating is measured by a measuring apparatus 618. The measurement result is transferred to a controller 620 controlling the coating head 616. As the controller 620 can utilize the result of the previous coating measurement (has a direct connection to the measuring apparatus of the previous coating, the controller or to the computer of the paper machine), the amount of the component of the last coating layer can be calculated as a difference of the latest and the previous measurement in a manner that is obvious to a person skilled in the art.

The same steps are also performed in the measurement which is to be performed from under the paper web. In that case, a measuring apparatus 622 measures the total amount of coating and transfers the measurement result to a controller 624. The controller 624 calculates the amount of the component of the last coating layer and controls a coating head 626. By means of a measuring apparatus 628, the amount of coating formed by a coating head 632 can also be measured, and, if necessary, the amount of coating can be adjusted by means of a controller 630. The process can be continued in this way, and the amount of components of more and more coating layers can be measured. The amount of component is measured as a surface density, the SI unit of which is $g/m^2$.

Let us now examine calibration measurement, which improves the operation of the apparatus. In the calibration measurement, M measurements are carried out in the MIR and NIR region at a desired wavelength band. The measurement at the i:th wavelength band, where i is i=1, ..., N, is carried out as follows. A measurement signal $U_i^{pap}$ which is proportional to the intensity of the i:th wavelength band of the paper or board coating is measured. A measurement signal $U_i^{ref}$ which is proportional to the intensity of the reference object with known properties is measured at a corresponding wavelength band. Then, paper or board 205, 311 to be measured is used instead of the reference object in FIGS. 2A, 2B, 3A. The absorbency $A_i$ of the i:th wavelength band is formed in the following manner:

$$A_i = -\log\left(\frac{U_i^{pap}}{U_i^{ref}}\right).$$

Since there are at least two components, the amount of j:th component $\hat{C}^j$ is formed as follows:

$$\hat{C}^j = b_{offset}^j + \sum_{i=1}^{N} b_i^j A_i,$$

where j is the index of each component. Weighting coefficients $b_{offset}^j$ and $b_i^j$ can be determined separately by determination measurements which use paper and board samples with known optical properties, containing each component. Since the properties of these objects of measurement are known, correct values for the amount $\hat{C}^j$ and the absorbency $A_i$ are known in advance in the determination measurements. By performing a number of measurements for each component by means of known objects of measurement, the weighting coefficients $b_{offset}^j$ and $b_i^j$ can be adjusted such that the results of the determination measurements and the results known in advance are statistically congruent. The coating measurement result is often not linear with respect to the amount of coating. The measurement results can thus be linearized by a polynomial of degree two for example in the following manner:

$C_w^j = a_1 \hat{C}^{j^2} + a_2 \hat{C}^j + a_3$. Coefficients $a_1$, $a_2$ and $a_3$ are selective such that the measurement response becomes linear. The total amount of coating $C_{wu}^j$ for one component is calculated by means of formula calculation for example in the following manner:

$$C_{wu}^j = \frac{C_w^j}{AC_j} \cdot 100\%,$$

where AC represents the component content (%) in the coating paste. When the coating contains several components, the total amount of coating $C_{wu}$ is calculated as follows:

$$C_{wu} = \frac{\sum_{j=1}^{N} C_w^j}{\sum_{j=1}^{N} AC_j} \cdot N \cdot 100\%,$$

where N represents the amount of components in the coating. In addition, to specify the measurement, offset and slope corrections obvious to a person skilled in the art can be performed.

When the weighting coefficients are determined, the calibration measurement can be performed with the objects of measurement, whereafter the measuring apparatus operates reliably without another calibration measurement. A checking measurement, wherein $U_i^{ref}$ is measured, is carried out at intervals under measuring conditions and, in order to eliminate the effect of changes occurred in the measuring apparatus, in the measurement result of the actual components.

Although the invention has been described above with reference to the example according to the attached drawings, it is obvious that the invention is not restricted thereto, but it can be modified in a variety of ways within the scope of the inventive idea disclosed in the attached claims.

That which is claimed:

1. A method for measuring a coating from paper or board by means of IR radiation, the coating comprising at least two components, said method comprising carrying out the measurement by one detector, measuring at least one component from the coating by using MIR radiation and at least one component being measured by using NIR radiation, wherein in order to measure at least one component by using MIR radiation said method comprises:
   directing IR radiation at the coating;
   chopping the IR radiation directed at the coating;
   bandpass filtering a MIR wavelength band of the component, which is sensitive to the absorption of at least one component from the IR radiation emerging from the coating;
   measuring the strength of the MIR radiation sensitive to the absorption;
   bandpass filtering a MIR wavelength band of the component, which is insensitive to the absorption of the component from the IR radiation emerging from the coating;
   measuring the strength of the MIR radiation insensitive to the absorption;
   measuring the strength of the absorption of the component by comparing the strength of the MIR radiation sensitive to the absorption and the strength of the MIR radiation insensitive to the absorption with each other; and
   determining the amount of at least one component of the coating on the basis of the measured strength of at least one MIR absorption; and,
   in order to measure at least one component by using NIR radiation said method further comprises:
   bandpass filtering a NIR wavelength band of the component, which is sensitive to the absorption of the component from the IR radiation emerging from the coating;
   measuring the strength of the NIR radiation sensitive to the absorption;
   bandpass filtering a NIR wavelength band of the component, which is insensitive to the absorption of the component from the IR radiation emerging from the coating;
   measuring the strength of the NIR radiation insensitive to the absorption;
   measuring the strength of the absorption of the component by comparing the strength of the NIR radiation sensitive to the absorption and the strength of the NIR radiation insensitive to the absorption with each other; and
   determining the amount of at least one component of the coating on the basis of the measured strength of at least one NIR absorption.

2. A method for measuring a coating from paper or board by means of IR radiation, the method comprising:
   measuring from the coating at least one component by using MIR radiation and at least one component by using NIR radiation, and, in order to measure at least one component by using MIR radiation said measuring comprising:
   directing IR radiation at the coating;
   chopping the IR radiation directed at the coating;
   bandpass filtering a MIR wavelength band of the component, which is sensitive to the absorption of at least one component from the IR radiation emerging from the coating;

measuring the strength of the MIR radiation sensitive to the absorption;

bandpass filtering a MIR wavelength band of the component, which is insensitive to the absorption of the component from the IR radiation emerging from the coating;

measuring the strength of the MIR radiation insensitive to the absorption;

measuring the strength of the absorption of the component by comparing the strength of the MIR radiation sensitive to the absorption and the strength of the MIR radiation insensitive to the absorption with each other; and determining the amount of at least one component of the coating on the basis of the measured strength of at least one MIR absorption; and, in order to measure at least one component by using NIR radiation said measuring comprises:

bandpass filtering a NIR wavelength band of the component, which is sensitive to the absorption of the component from the IR radiation emerging from the coating;

measuring the strength of the NIR radiation sensitive to the absorption;

bandpass filtering a NIR wavelength band of the component, which is insensitive to the absorption of the component from the IR radiation emerging from the coating;

measuring the strength of the NIR radiation insensitive to the absorption;

measuring the strength of the absorption of the component by comparing the strength of the NIR radiation sensitive to the absorption and the strength of the NIR radiation insensitive to the absorption with each other; and determining the amount of at least one component of the coating on the basis of the measured strength of at least one NIR absorption.

3. A method as claimed in claim 2, wherein said measuring of MIR and NIR radiation are performed using separate detectors.

4. A method as claimed in claim 2, wherein said measuring of MIR and NIR are performed using radiation reflected from the coating in the measurement direction, which is other than the direction of specular reflection.

5. A method as claimed in claim 2, wherein said chopping chops IR radiation emerging from the coating synchronously with IR radiation illuminating the coating.

6. A method as claimed in claim 2, wherein said chopping chops IR radiation illuminating the coating and IR radiation emerging from the coating with a disc-like chopper comprising teeth for preventing IR radiation from passing, and teeth gaps for allowing IR radiation to pass.

7. A method as claimed in claim 6, wherein said directing directs IR radiation at the coating such that an image of the surface emitting IR radiation is provided to the chopper and an image of an imaging lens is provided to the coating.

8. A method as claimed in claim 2, wherein said chopping and bandpass filtering IR radiation emerging from the coating with a disc-like chopper comprising MIR and NIR filters for allowing IR radiation to pass, and filter gaps for preventing IR radiation from passing.

9. A method as claimed in claim 8 further comprising adjusting the middle wavelength of the bandpass of MIR and NIR filters used in said bandpass filtering by the angle of inclination of the filters with respect to the direction of IR radiation penetrating the filters.

10. A method as claimed in claim 2 further comprises:

measuring, in order to calibrate the operation of the method in both the MIR and NIR region, a measurement signal $U_i^{pap}$ which is proportional to the intensity of the i:th wavelength band of the paper or board coating;

measuring a measurement signal $U_i^{ref}$ which is proportional to the intensity of the reference object with known properties at a corresponding wavelength band;

forming the absorbency $A_i$ of the i:th wavelength band in the following manner:

$$A_i = -\log\left(\frac{U_i^{pap}}{U_i^{ref}}\right);$$

and forming the amount of j:th component $\hat{C}^j$ as follows:

$$\hat{C}^j = b_{offset}^j + \sum_{i=1}^{N} b_i^j A_i,$$

where j is the index of each component, i is the index of the wavelength band used in the measurement and measurements are performed at N wavelength bands such that i runs from 1 to N.

11. A method as claimed in claim 2, wherein paper or board is coated several times, and wherein said method is performed before and after the paper or board is coated to measure the coating layer.

12. A method as claimed in claim 2, wherein said measuring using MIR radiation measures one or more coating components, selected from the group consisting of calcium carbonate, kaolin, silicon and water, , and said measuring using NIR radiation measures one or more components selected from the group consisting of kaolin, talc, gypsum, latex, starch, silicon and water, and, when water is measured, determining the moisture content.

13. A method as claimed in claim 12, wherein when calcium carbonate and kaolin are measured by means of MIR, the absorption of calcium carbonate is measured at a wavelength band with a middle wavelength of about 3950 nm, and the absorption of kaolin is measured by means of MIR radiation at a wavelength band with a middle wavelength of about 2700 nm.

14. A method as claimed in claim 12, wherein when kaolin and water are measured by means of NIR radiation, the absorption of kaolin is measured at a wavelength band with a middle wavelength of about 2208 nm, and the absorption of water is measured by means of NIR radiation at a wavelength band with a middle wavelength of about 1940 nm.

15. A method as claimed in claim 2, wherein said measuring by means of MIR and NIR radiation measure at least one wavelength band insensitive to the absorption of the component on both sides of the absorbing wavelength band, determine, on the basis of the measured results, the strength of the radiation insensitive to absorption, and compare the strength of the radiation sensitive to absorption and the formed strength of the radiation insensitive to absorption with each other, in order to determine the absorption strength.

16. A method as claimed in claim 2, wherein the measurement is performed by means of both MIR and NIR radiation to measure the absorption by means of the radiation strength, wherein said chopping comprises chopping the IR radiation directed at the coating such that during the illumination time, the coating is illuminated by IR radiation and during the off-period of illumination, the coating is not illuminated by IR radiation, said bandpass filtering comprises bandpass filtering the IR radiation emerging from the coating such that during detection time, the radiation from the coating is allowed to pass to the measurement, the detection time being longer than the illumination time, and during the off-period of the detection, the radiation from the coating is prevented from passing to the measurement, and wherein said measuring comprises:
  measuring a first interference level of the coating when radiation emerging from the coating is passed to the measurement during the detection time before the illumination time begins;
  measuring the strength of the total radiation comprising both the interference and the radiation to be measured when radiation emerging from the coating is passed to the measurement during the detection time and the coating is illuminated during the illumination time simultaneously;
  measuring a second interference level of the coating when radiation emerging from the coating is passed to the measurement during the detection time after the illumination time has ended;
  forming the interference level from the mean value of the first and second interference; and
  subtracting the averaged interference level from the strength of the total radiation.

17. A method as claimed in claim 2, said measuring by means of MIR and NIR radiation also measure IR radiation from the paper or board during a period when the coating is not illuminated with IR radiation and determine the temperature of paper or board from the measured IR radiation.

18. An apparatus for measuring a coating from paper or board by means of IR radiation, the coating comprising at least two components, wherein the apparatus comprises one detector for measuring at least one component from the coating by using MIR radiation and at least one component by using NIR radiation, the apparatus comprising:
  an optical power source for radiating IR radiation to the coating;
  a chopper for chopping the IR radiation directed at the coating;
  wherein in order to perform MIR measurement for one component the apparatus comprises:
    a bandpass filter for filtering a MIR wavelength band of the component, which is sensitive to the absorption of the component from the IR radiation emerging from the coating;
    a detector is arranged to detect MIR radiation sensitive to absorption and to convert the strength of the detected MIR radiation into an electrical signal of equal strength, by means of which signal the apparatus is arranged to measure the strength of the MIR radiation sensitive to absorption; and
    a bandpass filter for filtering a MIR wavelength band of the component, which is insensitive to the absorption of the component from the IR radiation emerging from the coating, wherein
      the detector is arranged to detect MIR radiation insensitive to absorption and to convert the strength of the detected MIR radiation into an electrical signal of equal strength, by means of which signal the apparatus is arranged to measure the strength of the MIR radiation insensitive to absorption;
    the apparatus is arranged to measure the strength of the absorption of the component by comparing the strength of the MIR radiation sensitive to absorption and the strength of the MIR radiation insensitive to absorption with each other; and
    the apparatus is arranged to determine the amount of at least one component of the coating on the basis of the measured strength of at least one MIR absorption; and,
  wherein in order to perform NIR measurement for one component the apparatus comprises:
    a bandpass filter for filtering a wavelength band of at least one other component, which is sensitive to the absorption of said at least one other component in the NIR region from the IR radiation emerging from the coating;
    the detector is arranged to detect NIR radiation sensitive to absorption and to convert the strength of the detected NIR radiation into an electrical signal of equal strength, by means of which signal the apparatus is arranged to measure the strength of the NIR radiation sensitive to absorption; and
    a bandpass filter for filtering a wavelength band of at least one other component, which is insensitive to the absorption of said at least one other component in the NIR region from the IR radiation emerging from the coating, wherein
      the detector is arranged to detect NIR radiation insensitive to absorption and convert the strength of the detected NIR radiation into an electrical signal of equal strength, by means of which signal the apparatus is arranged to measure the strength of the NIR radiation insensitive to absorption;
    the apparatus is arranged to measure the strength of the absorption of the component by comparing the strength of the NIR radiation sensitive to absorption and the strength of the NIR radiation insensitive to absorption with each other;
    the apparatus is arranged to determine the amount of at least one component of the coating on the basis of the measured strength of at least one NIR absorption.

19. An apparatus as claimed in claim 18, wherein said detector is arranged to measure the radiation reflected from the coating in the measurement direction, which is other than the direction of specular reflection.

20. An apparatus as claimed in claim 18, wherein the apparatus further comprises a chopper for chopping the IR radiation emerging from the coating synchronously with the IR radiation illuminating the coating.

21. An apparatus as claimed in claim 20, wherein said chopper for chopping the IR radiation illuminating the coating and IR radiation emerging from the coating is a disc-like chopper comprising teeth for preventing IR radiation from passing, and teeth gaps for allowing IR radiation to pass.

22. An apparatus as claimed in claim 21, wherein the disc-like chopper comprises MIR and NIR filters as bandpass filters for allowing IR radiation to pass, and filter gaps for preventing IR radiation from passing, whereby the disc-like chopper is arranged to chop and bandpass filter the IR radiation emerging from the coating.

23. An apparatus as claimed in claim 20, wherein the apparatus is arranged to direct IR radiation at the coating such that an image of the surface emitting IR radiation is provided to the chopper and an image of an imaging lens is provided to the coating.

24. An apparatus as claimed in claim 18, wherein in order to calibrate the operation of the apparatus, the apparatus is arranged to measure in both the MIR and NIR region a measurement signal $U_i^{pap}$ which is proportional to the intensity of the i:th wavelength band of the paper or board coating; the apparatus being arranged:

to measure a measurement signal $U_i^{ref}$ which is proportional to the intensity of the reference object with known properties at a corresponding wavelength band;

to form the absorbency $A_i$ of the i:th wavelength band in the following manner:

$$A_i = -\log\left(\frac{U_i^{pap}}{U_i^{ref}}\right);$$

to form the amount of j:th component $\hat{C}^j$ as follows:

$$\hat{C}^j = b_{offset}^j + \sum_{i=1}^{N} b_i^j A_i,$$

where j is the index of each component, i is the index of the wavelength band used in the measurement, and measurements are performed at N wavelength bands such that i runs from 1 to N.

25. An apparatus as claimed in claim 18, wherein the middle wavelength of the bandpass of the MIR and NIR filters is adjustable by changing the angle of inclination of the filters with respect to the direction of IR radiation penetrating the filters.

26. An apparatus as claimed in claim 18, wherein the apparatus comprises several apparatus units and when paper or board is coated several times, each apparatus unit is arranged to measure a coating layer before and/or after each coating operation.

27. An apparatus as claimed in claim 18, wherein the apparatus is arranged to measure one or more coating components selected from the group consisting of calcium carbonate, kaolin, silicon and water, by using MIR radiation, and the apparatus is arranged to measure one or more components selected from the group consisting of kaolin, talc, gypsum, latex, starch, silicon and water, by using NIR radiation, and, when water is measured, the apparatus is arranged to determine the moisture content.

28. An apparatus as claimed in claim 27, wherein when calcium carbonate and kaolin are measured, the apparatus is arranged to measure the absorption of calcium carbonate at a wavelength band with a middle wavelength of about 3950 nm by means of MIR radiation, and the apparatus is arranged to measure the absorption of kaolin at a wavelength band with a middle wavelength of about 2700 nm by means of MIR radiation.

29. An apparatus as claimed in claim 27, wherein when kaolin and water are measured, the apparatus is arranged to measure the absorption of kaolin at a wavelength band with a middle wavelength of about 2208 nm by means of NIR radiation, and the apparatus is arranged to measure the absorption of water at a wavelength band with a middle wavelength of about 1940 nm by means of NIR radiation.

30. An apparatus as claimed in claim 18, wherein in the measurements performed by means of both MIR and NIR radiation, the apparatus is arranged to measure at least one wavelength band insensitive to the absorption of the component on both sides of the absorbing wavelength band and to form, on the basis of the measured results, the strength of the radiation insensitive to absorption, and, in order to determine the absorption strength, to compare the strength of the radiation sensitive to absorption and the formed strength of the radiation insensitive to absorption with each other.

31. An apparatus as claimed in claim 18, wherein in the measurements performed by means of both MIR and NIR radiation to measure the absorption by means of the radiation strength, the apparatus is arranged to chop the IR radiation directed at the coating such that during the illumination time, the coating is illuminated by IR radiation and during the off-period of illumination, the coating is not illuminated by IR radiation;

to chop the IR radiation emerging from the coating such that during detection time, the radiation from the coating is allowed to pass to the measurement, the detection time being longer than the illumination time, and during the off-period of the detection, the radiation from the coating is prevented from passing to the measurement;

when radiation emerging from the coating is passed to the measurement during the detection time before the illumination time begins, to measure a first interference level of the coating;

when radiation emerging from the coating is passed to the measurement during the detection time and the coating is illuminated during the illumination time simultaneously, to measure the strength of the total radiation comprising both the interference and the radiation to be measured;

when radiation emerging from the coating is passed to the measurement during the detection time after the illumination time has ended, to measure a second interference level of the coating;

to form the interference level from the mean value of the first and second interference; and to subtract the averaged interference level from the strength of the total radiation.

32. An apparatus as claimed in claim 18, wherein the apparatus is also arranged to measure the IR radiation of paper or board during the off-period of illumination, when the coating is not illuminated with IR radiation, and the apparatus is arranged to determine the temperature of paper or board from the measured IR radiation.

33. An apparatus for measuring a coating from paper or board by means of IR radiation, the coating comprising at least two components, wherein the apparatus is arranged to simultaneously measure at least one component from the coating by using MIR radiation and at least one component by using NIR radiation, the apparatus comprising:

an optical power source for radiating IR radiation to the coating;

a chopper for chopping the IR radiation directed at the coating; and, wherein in order to perform MIR measurement for one component the apparatus comprises:

a bandpass filter for filtering a MIR wavelength band of the component, which is sensitive to the absorption of the component from the IR radiation emerging from the coating;

a first detector for detecting MIR radiation sensitive to absorption and converting the strength of the detected MIR radiation into an electrical signal of equal strength, by means of which signal the apparatus is arranged to measure the strength of the MIR radiation sensitive to absorption; and a bandpass filter for filtering a MIR wavelength band of the component, which is insensitive to the absorption of the component from the IR radiation emerging from the coating, wherein the first detector is arranged to detect MIR radiation insensitive to absorption and to convert the strength of the detected MIR radiation into an electrical signal of equal strength, by means of which signal the apparatus is arranged to measure the strength of the MIR radiation insensitive to absorption;

the apparatus is arranged to measure the strength of the absorption of the component by comparing the strength of the MIR radiation sensitive to absorption and the strength of the MIR radiation insensitive to absorption with each other;

the apparatus is arranged to determine the amount of at least one component of the coating on the basis of the measured strength of at least one MIR absorption; and, wherein in order to perform NIR measurement for one component the apparatus comprises:

a bandpass filter for filtering a wavelength band of at least one other component, which is sensitive to the absorption of said at least one other component in the NIR region from the IR radiation emerging from the coating;

a second detector for detecting NIR radiation sensitive to absorption and converting the strength of the detected NIR radiation into an electrical signal of equal strength, by means of which signal the apparatus is arranged to measure the strength of the NIR radiation sensitive to absorption; and a bandpass filter for filtering a wavelength band of at least one other component, which is insensitive to the absorption of said at least one other component in the NIR region from the IR radiation emerging from the coating, wherein the second detector is arranged to detect NIR radiation insensitive to absorption and convert the strength of the detected NIR radiation into an electrical signal of equal strength, by means of which signal the apparatus is arranged to measure the strength of the NIR radiation insensitive to absorption;

the apparatus is arranged to measure the strength of the absorption of the component by comparing the strength of the NIR radiation sensitive to absorption and the strength of the NIR radiation insensitive to absorption with each other; and the apparatus is arranged to determine the amount of at least one component of the coating on the basis of the measured strength of at least NIR absorption.

* * * * *